(12) United States Patent
Sarvazyan et al.

(10) Patent No.: US 6,981,945 B1
(45) Date of Patent: Jan. 3, 2006

(54) COLONOSCOPE HANDGRIP WITH FORCE AND TORQUE MONITOR

(75) Inventors: Armen Sarvazyan, Lambertville, NJ (US); Louis Y. Korman, Rockville, MD (US); Sergey Tsyuryupa, Levittown, PA (US)

(73) Assignee: Artann Laboratories, Inc., Lambertville, NJ (US)

( * ) Notice: Subject to any disclaimer, the term of this patent is extended or adjusted under 35 U.S.C. 154(b) by 0 days.

(21) Appl. No.: 10/986,662

(22) Filed: Nov. 12, 2004

(51) Int. Cl.
*A61B 1/00* (2006.01)

(52) U.S. Cl. .......................................... 600/131; 606/1
(58) Field of Classification Search ................ 600/101, 600/117, 118, 131; 606/1; 434/262
See application file for complete search history.

(56) References Cited

U.S. PATENT DOCUMENTS

| | | | |
|---|---|---|---|
| 4,366,810 A | 1/1983 | Slanetz | |
| 4,469,091 A | 9/1984 | Slanetz | |
| 5,275,151 A | 1/1994 | Shockey | |
| 5,290,279 A | 3/1994 | Bonati | |
| 5,333,603 A | 8/1994 | Schuman | |
| 5,531,687 A | 7/1996 | Snoke | |
| 5,785,644 A | 7/1998 | Grabover | |
| 5,910,105 A | 6/1999 | Swain | |
| 6,428,530 B1 | 8/2002 | Matern | |
| 6,540,737 B2 | 4/2003 | Bacher | |
| 6,594,552 B1 * | 7/2003 | Nowlin et al. ............... 700/260 |
| 6,929,481 B1 * | 8/2005 | Alexander et al. .......... 434/262 |
| 2003/0212308 A1 * | 11/2003 | Bendall ...................... 600/131 |
| 2004/0220449 A1 * | 11/2004 | Zirps et al. ................. 600/104 |
| 2005/0069854 A1 * | 3/2005 | Maier .......................... 434/262 |

\* cited by examiner

*Primary Examiner*—Beverly M. Flanagan
(74) *Attorney, Agent, or Firm*—Boris Leschinsky

(57) ABSTRACT

A handgrip for a colonoscope shaft capable of measuring and presenting to the operator of radial and longitudinal forces applied by the operator during the manipulation with the colonoscope. The handgrip includes an internal sleeve positioned over the shaft of the colonoscope so that it can be released and repositioned by depressing a release button. And external sleeve covers the internal sleeve and provides for a convenient grip by the operator. The only means of transmission of force applied by the operator from the external sleeve to the internal sleeve is the engaging means such as a flexible rectangular bar or a set of engaging plates imbedded between the external sleeve and internal sleeve. The engaging means are equipped with a set of sensors such as strain gages positioned on all sides of the bar to measure the forces between the sleeves, which correspond to the forces applied by the operator to the shaft of the colonoscope. The measurements are then transmitted to an electronic unit for data processing and then further to a display system such as a personal computer.

20 Claims, 15 Drawing Sheets

COLONOSCOPE HANDGRIP WITH FORCE AND TORQUE MONITOR

BACKGROUND OF THE INVENTION

The present invention relates generally to devices useful for insertion of steerable catheters and scopes. More particularly, the invention describes a handgrip to be positioned over the shaft of the scope such as a colonoscope allowing to measure and display insertion forces and torque throughout the procedure.

In many cases, it has been desirable to examine internal organs, passages and the like of the human body for purposes of diagnosis, biopsy, and therapeutic interventions. One method of examining the internal organs of the patient without major surgery is to insert a remote sensing device such as an endoscope into the body through a natural body orifice such as colon or a specially prepared surgical opening.

The primary area of application of the invention is for use with a colonoscope but other devices can also be used with the handgrip of the invention. Therefore, the word "colonoscope" is used throughout this description to broadly include various types of direct vision and fiberoptic endoscopes, fiberscopes, arthoscopes, laparoscopes, and other types or steerable and deflectable catheters and tubes designed to be inserted into tight openings and curved passages.

The use of steerable scopes for internal examination is not limited to medicine. Remote sensing devices can be used to examine the interior of otherwise inaccessible mechanical structures without opening them; such as aircraft wings, the walls of buildings, and the enclosed areas of any structure. In these cases, an internal examination, without putting a major opening in the structure, can help to determine the reason for mechanical failure or the level of corrosion levels.

The preferred area of interest for the device of the present invention is in medicine, and more particularly in colonoscopy. Colonoscopy is the preferred method to screen for colorectal cancer, a disease that afflicts 115,000 patients/year in the US. Several million screening, diagnostic and therapeutic colonoscopies are performed each year in the U.S. hospitals and ambulatory surgery centers. Colonoscopy requires a physician to inspect the colonic mucosal surface by applying force to a colonoscope and advancing this flexible tube through a series of stationary and movable colonic loops.

When using a colonoscope, a common problem is to be able to maneuver the inspection end of the scope and position it in proximity to the area of interest. This maneuvering is performed by a trained operator who uses a combination of visual inspection of images and tactile coordination to maneuver through the twists and turns found in the colon. The operator will subjectively sense the resistance to maneuvers by the "feel" of the instrument and anticipate the amount of force necessary to advance the device forward. The application of force to the colon and its anatomic attachments can be painful. Particularly undesirable is the frequent occurrence of excessive contact pressure on an internal tissue, which can result in perforation. Sedation with analgesia is frequently required to make the procedure comfortable. Preliminary studies suggest that there is significant variation in the forces applied and that these forces can be excessive. Operator training programs are designed to reduce the variation in technique, however training metrics remain subjective and the characterization of effective, less forceful insertion methods is not yet available. The need therefore exists to provide a device allowing an effective, low-cost method to define best practices and to implement these practices as part of training, ongoing education and quality assurance.

There is an extensive array of surgical instruments, catheters and endoscopes that can be introduced and guided into and through both solid and hollow organ systems such as gastrointestinal tract, blood vessels and heart, urologic and gynecologic systems. These devices are designed to perform a variety of functions such as illumination, introduction of radiographic contrast materials and other fluids, surgical therapies, dilation, etc.

Examples of such guiding or steering techniques and systems for catheters may be seen in U.S. Pat. No. 4,983,165 to Loiterman entitled "Guidance System For Vascular Catheter Or The Like," U.S. Pat. No. 4,776,844 to Ueda entitled "Medical Tube," U.S. Pat. No. 4,934,340 to Ebling et al. entitled "Device For Guiding Medical Catheters and Scopes," U.S. Pat. No. 4,930,521 to Metzget et al. entitled "Variable Stiffness Esophageal Catheter," U.S. Pat. No. 3,470 to Barchilon entitled "Dirigible Catheter," U.S. Pat. No. 3,605,725 to Bentov entitled "Controlled Motion Devices," and the Patent Cooperation Treaty ("PCT") Patent Application No. PCT W088/00810 of Tenerz et al. entitled "Guide For Mechanical Guiding Of A Catheter In Connection With Cardio And Vessel Examination." These catheters, however, failed to give the operator sufficient control of the distal end of the catheter and made it difficult to manipulate the distal end for specific isolation on particular sections of the body vessel or cavity.

Other steerable catheters or systems have been made to try to give the physician control of the use of the catheter during surgical procedures wherein fluids and the various tools are needed for the operation by providing a flexible tube for controlling the direction of movement of the distal end of the catheter. Examples of these other attempts may be seen in the PCT Patent Application No. PCTW091/11213 of Lundquist et al. entitled "Catheter Steering Mechanism," European Patent Application No. 370,158 of Martin entitled "Catheter For Prolonged Access," and U.S. Pat. No. 4,737,142 to Heckele entitled "Instrument For Examination And Treatment Of Bodily Passages." These devices, however, still failed to provide the control and manipulation of the catheter needed for use with the surgical tools and fluids required for an operation.

The need therefore exists for a handheld force measuring attachment device to be mounted on the colonoscope tube. This handgrip device is desirable to be easy to use, inexpensive to manufacture and result in less painful and safer colonoscopies.

SUMMARY OF THE INVENTION

Accordingly, it is an object of the present invention to overcome these and other drawbacks of the prior art by providing a novel handgrip for a colonoscope or a similar instrument that indicates to an operator the levels of force and torque developed during the manipulation of the colonoscope.

It is another object of the present invention to provide a force and torque indicating handgrip, which can be easily used with a variety of commercially available scope instruments.

It is a further object of the present invention to provide a handgrip adapted for sliding along the shaft of the colonoscope during its insertion and removal so that the area of grip by the hand of the operator can be changed depending on the clinical necessity.

It is yet a further object of the present invention to provide a handgrip, which can be reused multiple times and can withstand disinfection and sterilization by all commonly used methods without the loss of sensitivity or any undesirable change in force and torque indication.

The handgrip of the invention consists of an internal sleeve and an external sleeve slidingly positioned about the internal sleeve. An engaging means are positioned between both sleeves. As a result of that arrangement, in order to manipulate the colonoscope, the operator has to apply the necessary force and torque to the external sleeve of the device, which then transmits that force and torque through the engaging means first to the internal sleeve and then further to the colonoscope shaft itself. Sensor means are incorporated with the engaging means so that these forces can be accurately measured at the point of the engaging means and this measurement will correspond to the force and torque applied by the operator to the colonoscope shaft. That data is then transmitted to an indication device such as a PC or a visual display after an appropriate data processing.

In order to place the handgrip of the invention over the shaft of the colonoscope, provisions are made to allow both sleeves to be opened and closed such as with a clam-shell design. Alternatively, the shaft can be passed through the solid body handgrip prior to the procedure. Another contemplated alternative is to make a rigid opening in both sleeves such as in a C-shaped cross-section to then pass the shaft into the handgrip from a side.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF THE FIRST PREFERRED EMBODIMENT OF THE INVENTION

Colonoscopy procedure will now be briefly described. Colonoscopy requires that push/pull and torque forces be applied to the instrument to advance it through the colon. The forces applied account for the two most important limitations of colonoscopy: pain and colonic perforation. Conscious and deep sedation is used to control pain and the anxiety associated with anticipation of pain and is administered as a combination of an analgesic and sedative. Sedation enables the patient to tolerate greater forces applied by the operator to advance the instrument. There is significant variability in the amount of sedation used with some operators requiring little or no sedation and others using deep sedation. These observations suggest that the technical performance of the endoscopy is critically important in causing pain. In addition, perforation is the most serious complication of colonoscopy. The reported rate of colonic perforations varies widely and is estimated to be 0.01 to 0.3%. Perforations occur in both diagnostic and therapeutic procedures.

The structure, position and relation of the colon to the peritoneum and other organs affect the performance of the colonoscopy. Specific factors influencing the success of the procedure include: redundancy of colonic loops, presence of adhesions, prior surgery, acute angulation and stenosis with or without diverticular disease. The colon does loop in a variety of configurations and the force applied to the colonoscope may result in forward motion or a lateral force that is often associated with pain. Prior surgery frequently restricts mobility and increases the force required to traverse a particular part of the colon. Acute angulation is found in the recto-sigmoid, splenic and hepatic flexures and requires operators to increase push/pull and torque force to advance the instrument. The application of force against the wall of the colon can be substantial. Finally, stenosis or narrowing can be encountered and this often restricts the mobility adds to the angulation and distorts colonic configuration. In general, patient discomfort is considered a measure of force applied and increases in pain are likely to represent excess force.

A detailed description of the present invention now follows with reference to accompanying drawings in which like elements are indicated by like reference letters and numerals.

Figure 1:
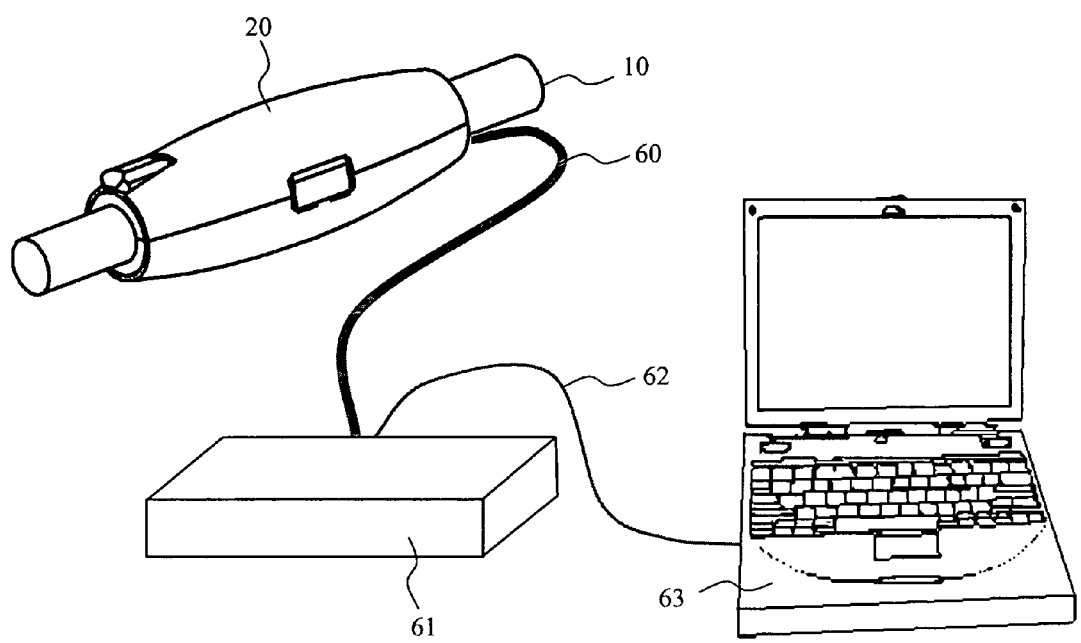
FIG. 1 is a general outline of the system of the invention including a handgrip and data processing elements.

A general block-diagram of the handgrip is shown on FIG. 1. The handgrip 20 is shown placed around a shaft or the tube 10 of the colonoscope. Note that only a small portion of the shaft is shown on the drawing in the vicinity of the grip area for the operator to handle the device. The handgrip is equipped with force and torque sensor means (as will be described in more detail below). The data from the sensor means is transmitted via a cable 60 to an electronic unit 61 for initial data processing, following by a second transmission via a cable 62 to a personal computer 63 or another display apparatus for a presentation of data to the operator. As can be well appreciated by those skilled in the art, wireless transmission of data from the handgrip to the electronic unit and then to the computer is also possible and will fall within the scope of the invention. In an alternate configuration, a separate data presentation window is incorporated into the image display of the colonoscope device itself. This configuration is especially beneficial for integrated devices when the handgrip of the invention is a part of the entire colonoscope setup.

Figure 2:
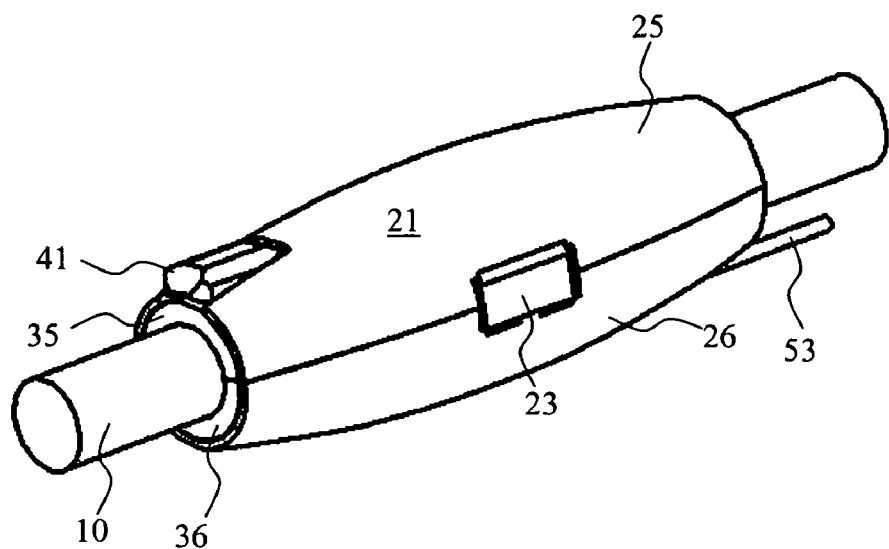
FIG. 2 is a view of the handgrip assembly according to the first embodiment of the invention.
Figure 3:
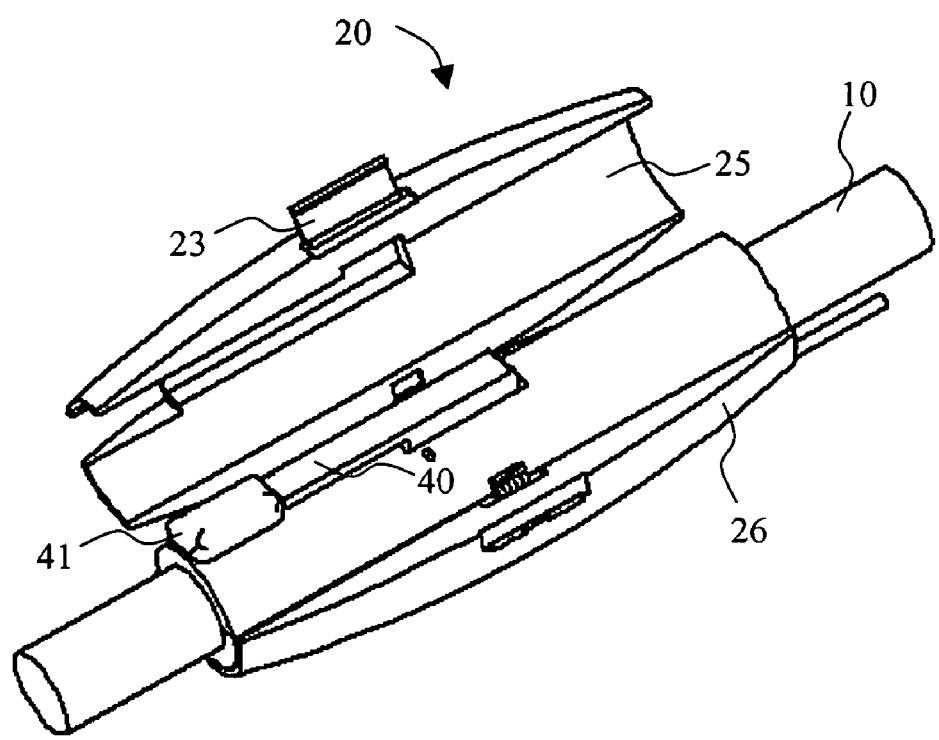
FIG. 3 is a view of the same but with the external sleeve opened.
Figure 4:
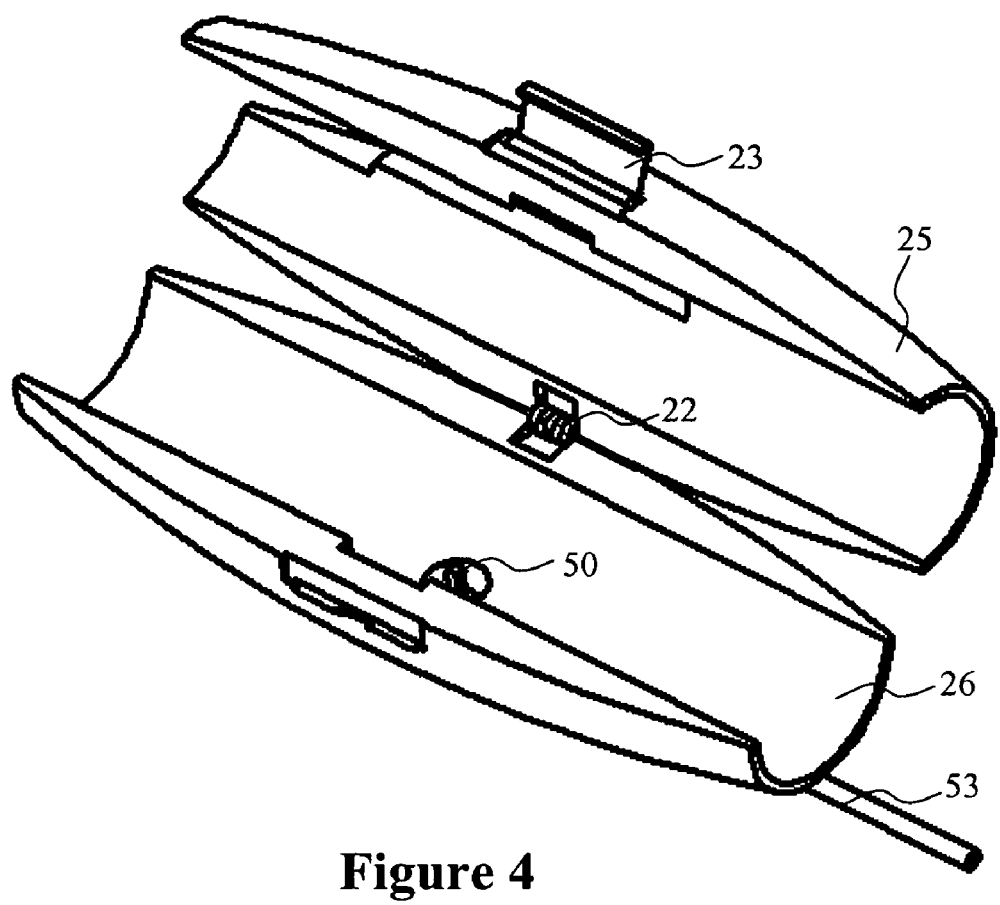
FIG. 4 is a view of just the external sleeve in its opened position.
Figure 5:
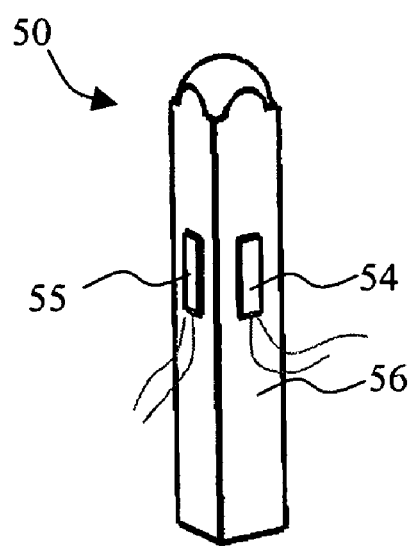
FIG. 5 is a view of the engaging and sensor means of the first embodiment of the invention.
Figure 6:
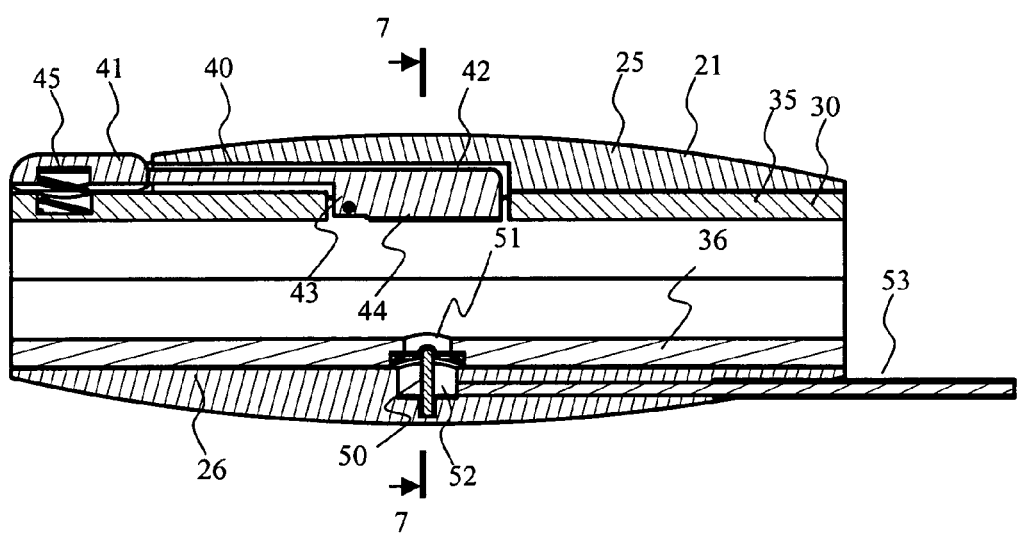
FIG. 6 is a side cross-sectional view of the handgrip assembly according to the first embodiment of the invention.
Figure 7:
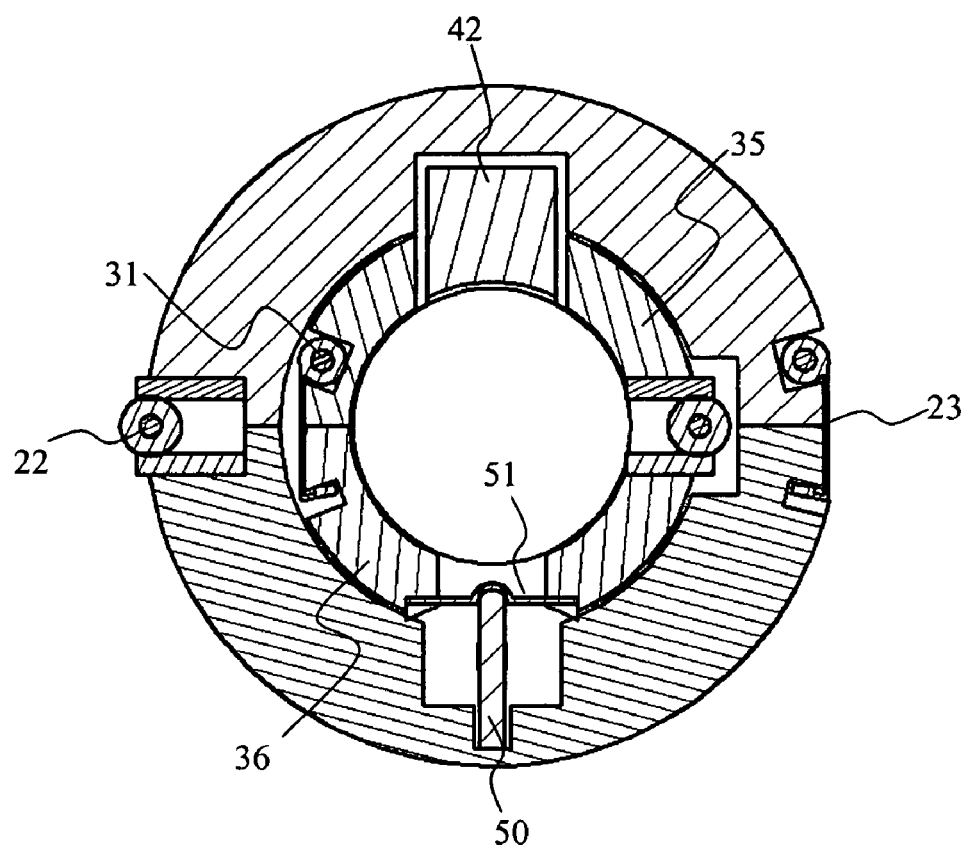
FIG. 7 is a cross-sectional view along the line 7—7 on FIG. 6.
Figure 8:
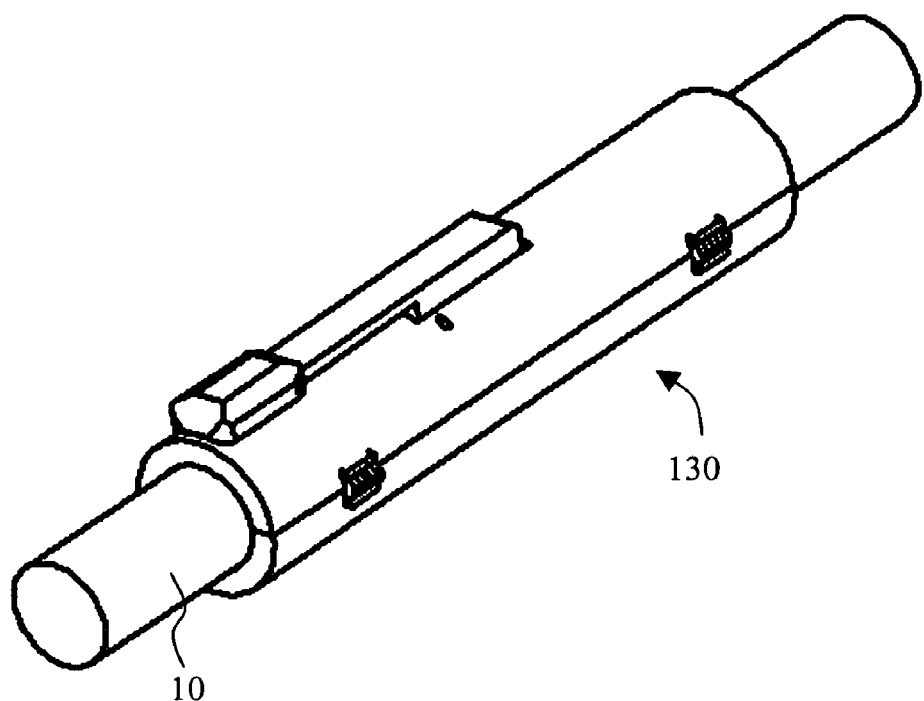
FIG. 8 is a view of the internal sleeve assembly according to the second embodiment of the invention.
Figure 9:
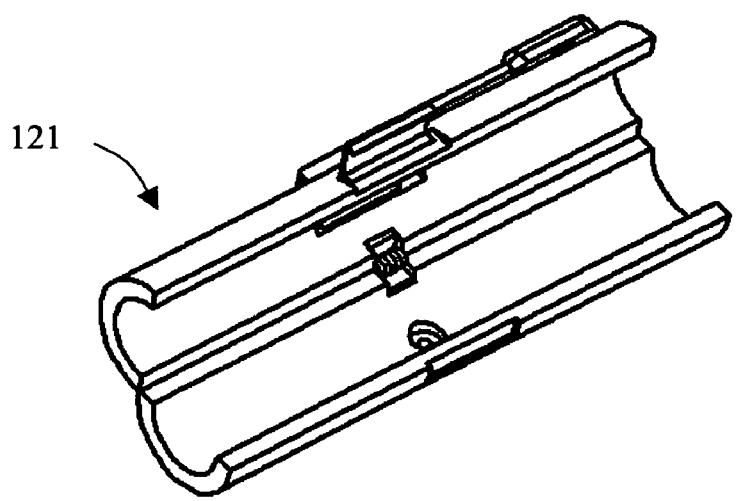
FIG. 9 is a view of the external sleeve of the second embodiment in its open position.
Figure 10:
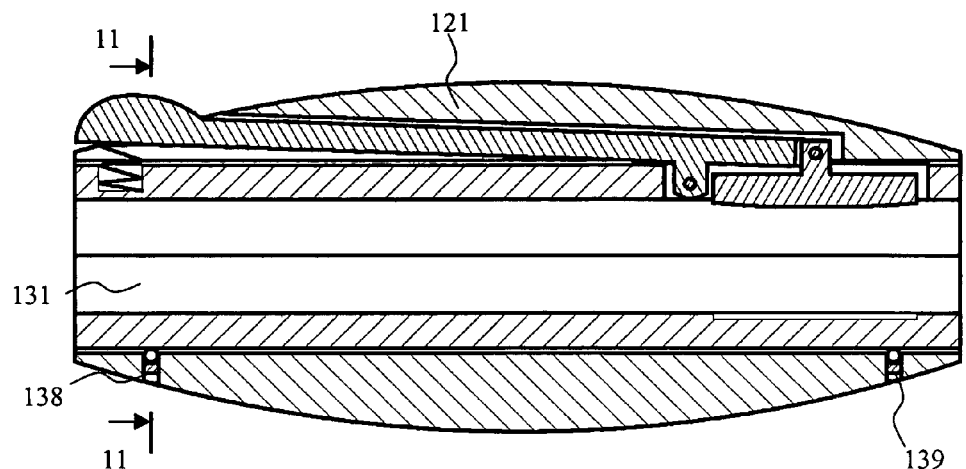
FIG. 10 is cross-sectional view of the assembly of the handgrip of the second embodiment of the invention, engaging and sensor means are not shown.
Figure 11:
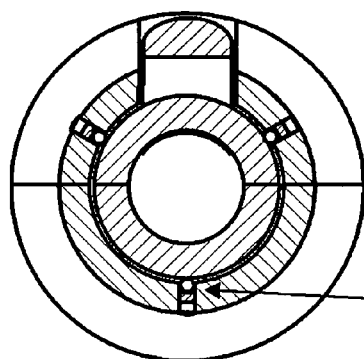
FIG. 11 is a cross-sectional view along the line 11—11 on FIG. 10.
Figure 12:
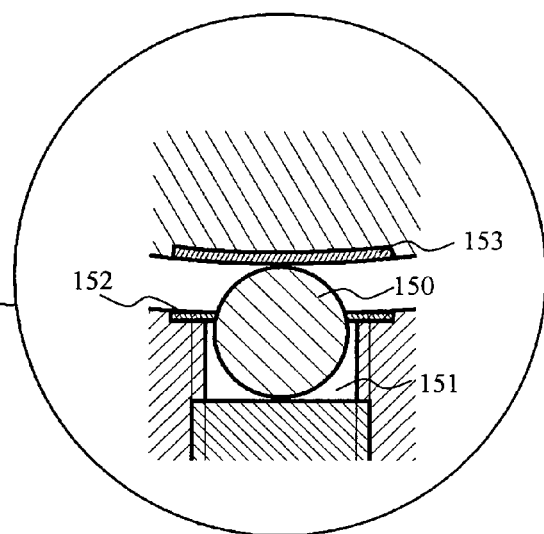
FIG. 12 is the enlarged depiction of the detail shown on FIG. 11.

The handgrip 20 will now be described in more detail. The first embodiment of the handgrip is shown in greater detail on FIGS. 2–7. The handgrip 20 consists of an external sleeve 21 slidingly positioned over an internal sleeve 30 with an engaging means 50 located therebetween. The external sleeve 21 has a shape adapted for easy grip by a human hand as shown on FIGS. 2 and 6. In its preferred configuration, the shape of the external sleeve is such that it covers almost entirely the internal sleeve 30 so that the operator holds the entire device only by the external sleeve. To allow its placement over the shaft 10 of the colonoscope, the external sleeve 21 is made in two halves 25 and 26 connected together on one side by a spring 22 biased in a way as to allow them to open when the clamp 23 is released. The spring 22 is also positioned to allow one half of the external sleeve to swing away and towards another. Alternatively, the halves 25 and 26 may be molded from a polymer material with a living hinge therebetween.

The internal sleeve 30 in turn also consists of two halves 35 and 36 connected together on one side by a hinge 31. There is no need for a clamp on the opposite side to keep both halves together as they are retained by an external sleeve 21. The shape of the sleeves is such that they fit entirely inside the external sleeve 21. The internal sleeve may therefore be positioned over the colonoscope shaft and engaged therewith.

Release button 40 is incorporated into the internal sleeve 30 so that the handgrip can be released from the shaft 10 of the colonoscope and moved over to a new location. The release button 40 is designed to constantly engage the shaft with a rough surface 44 of the retention lever 42, which in turn is pushed towards the shaft 10 by a spring 45 via a hinge 43. This can be generally referred to as a "normally closed" position, meaning a position in which the device is continuously engaged with the shaft of the colonoscope unless the release button is depressed. The button 45 is exposed through a cutout in the external sleeve so that the operator can depress it and release the surface 44 from the shaft 10. When the button 45 is released, the spring again pushes the lever 42 towards the shaft surface and the internal sleeve is therefore locked to the colonoscope shaft.

The external sleeve 21 and the internal sleeve 30 both have provisions to hold an engaging means 50 therebetween. Depressions 51 and 52 in the internal sleeve 36 and the external sleeve 26 respectively are envisioned to hold the engaging means 50 between the two sleeves. In its preferred configuration, the engaging means 50 is a flexible steel rectangular bar 56 with two pairs of strain gages 55 and 54 attached to the sides thereof and forming a sensor means capable of measuring perpendicular forces applied to the bar 56. Electrical wires carry out the signals from the strain gages 54 and 55 and are assembled together in a cable 53.

The bar 56 rigidly connects the external sleeve 21 to the internal sleeve 30. The operator holds the external sleeve while the shaft is attached to the internal sleeve. Force applied along the shaft of the colonoscope is measured by the first pair of strain gages while torque is measured by the second one.

In use, the handgrip is first placed over the shaft of the colonoscope by opening the external and internal sleeves and positioning them over the shaft. The internal sleeve is closed first following by the closure of the external sleeve. The device now is ready for force measurement. As the colonoscope is advanced by the operator, the longitudinal force is measured and displayed on the PC or another display device for the operator by having the sensor means recording the force from a first pair of strain gages 54 (or 55 depending on the orientation of the bar 56). At the same time, the torsion force is measured by the second pair of strain gages and displayed at the same time to the operator.

Provisions can be made to allow operator to set alarm conditions so that when the force or torque reach predetermined limit, the audio or visual alarm signal is generated.

DETAILED DESCRIPTION OF THE SECOND PREFERRED EMBODIMENT OF THE INVENTION

The second embodiment of the invention is shown in more detail on FIGS. 8–12. Note that the engaging means 50 is not shown. Design of this embodiment is similar to that of the first embodiment. The main difference is that the suspension of the internal sleeve 131 inside the external sleeve 121 is done using two spaced apart sets of three ball bearings 138 and 139. Each set has three balls 150 spaced preferably equally apart along the periphery of the internal sleeve forming these three ball bearings. Each ball 150 is set in its cavity 151 inside the external sleeve 121 and held in place by a retaining plate 152 while allowing the ball to protrude towards the running plate 153 on the internal sleeve 131.

The purpose of the ball bearings in this embodiment is to suspend the internal sleeve inside the external sleeve in a manner so that all torque and force are transmitted from the external to the internal sleeve only by the sensor means and not by friction between the sleeves.

The operation of the second embodiment is the same as that of the first embodiment.

DETAILED DESCRIPTION OF THE THIRD PREFERRED EMBODIMENT OF THE INVENTION

Figure 13:
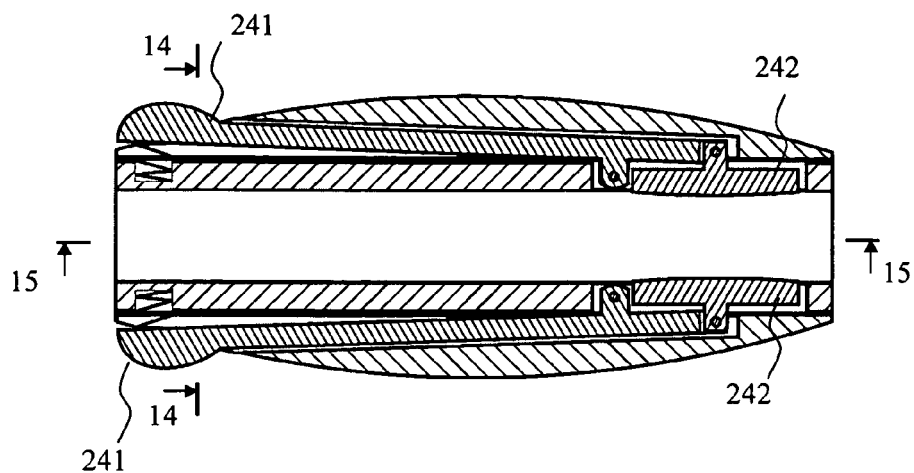
FIG. 13 is a longitudinal cross-sectional view of the third embodiment of the invention.
Figure 14:
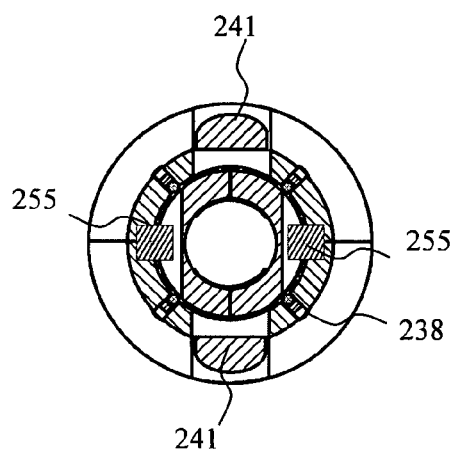
FIG. 14 is a cross-section along the line 14—14 on FIG. 13.
Figure 15:
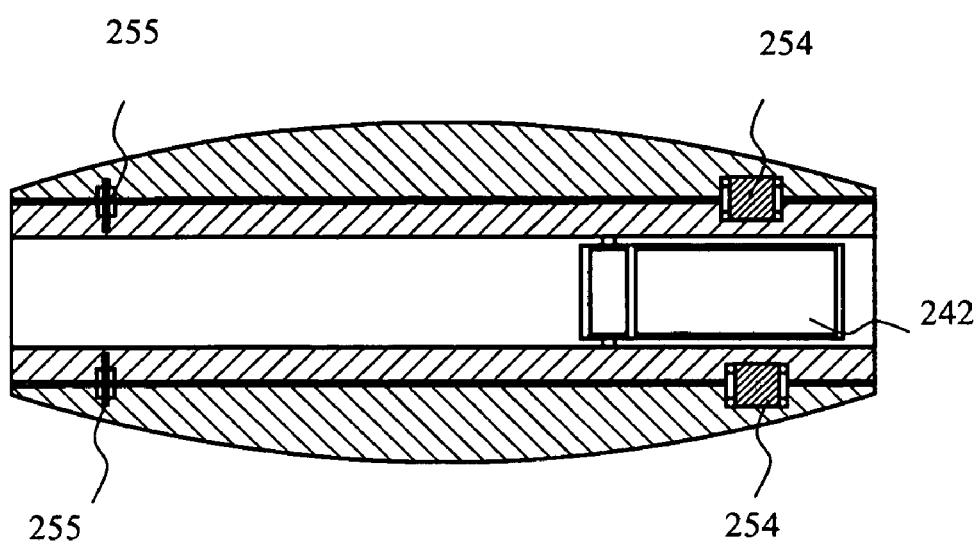
FIG. 15 is a longitudinal cross-section along the line 15—15 on FIG. 13.

The details of the third embodiment of the invention are shown in FIGS. 13–15. The main difference is in the design of the release buttons, engaging means, and the internal sleeve suspension means. The release button is made of two symmetrical parts 241 supported by the springs in a "normally closed" or engaged position in a manner similar to that described for the first embodiment of the invention. The advantage of this symmetrical arrangement is that the grip of the colonoscope shaft is ensured by levers 242 compressing the shaft from both sides rather than from one, which avoids slipping. Also, it makes for a better control of the release buttons by the operator.

Figure 13A:
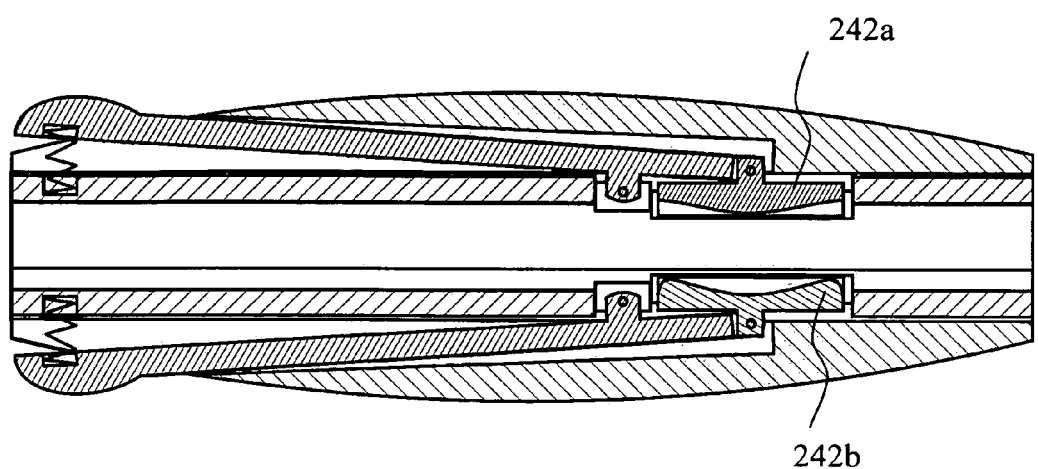
FIG. 13A is a longitudinal cross-section of an alternative design of the third embodiment of the invention.

FIG. 13A shows an alternate design of the shaft engaging mechanism comprising a pair of concave and convex levers 242a and 242b forming a depression for the colonoscope shaft. In that case, the shaft of the colonoscope is slightly bent when placed in the depression formed by the retaining levers 242*a* and 242*b*. This further reduces the possibility of inadvertent slipping of the shaft inside the handgrip during manipulations thereof.

The engaging means according to the third embodiment is arranged as a combination of radial 254 and longitudinal 255 sets of engaging plates. Each plate is equipped with a sensor to measure its deflection as a function of force applied to one side of this plate. Strain gage sensors can be used advantageously for this purpose along with other sensors known in the art. Application of longitudinal force such as for the purpose of advancing the colonoscope would cause the longitudinal set of plates 255 to bend, which will be detected and recorded by the sensors. Rotation of the shaft will correspondingly cause the radial set of plates 254 to bend as will be captured by their sensors. Therefore, the entire picture of force and torque application can be accurately monitored. As shown on the drawings, the two sets of plates could be extended to be positioned at the opposite ends of the handgrip but that is not absolutely necessary for the accurate function of the device.

Finally, the internal sleeve support system includes two sets of four ball bearings each, which further reduces the friction component of the force transfer from the external sleeve to the internal sleeve and makes the force measurement more accurate.

Figure 14A:
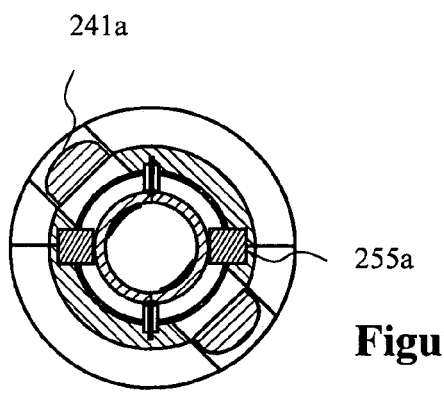
FIG. 14A is a cross-section of the alternate design of the third embodiment taken along line 14—14 on FIG. 13.

FIG. 14A illustrates an alternate design of the engaging means comprising a front and a rear set of four plates 255*a* each. In that case, the internal sleeve is supported by plates 255*a* at four points in the front and four points in the rear part of the external sleeve, which improves the torque and force measurement results and obviates the need for additional suspension bearings. The release button 241*a* is preferably arranged at a 45-degree angle to the planes defined by the plates 255*a* so that there is no interaction between the release mechanism and the engaging means of the handgrip.

DETAILED DESCRIPTION OF THE FOURTH PREFERRED EMBODIMENT OF THE INVENTION

Figure 16:
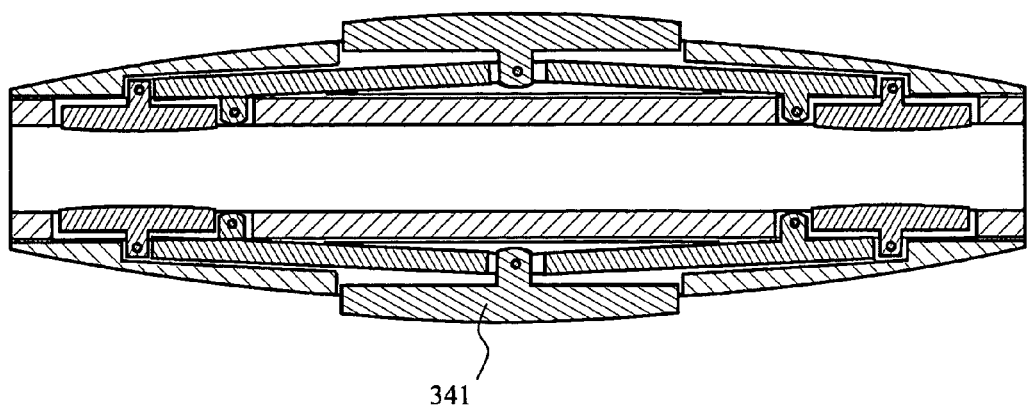
FIG. 16 is a longitudinal cross-section of the fourth embodiment of the invention.
Figure 17:
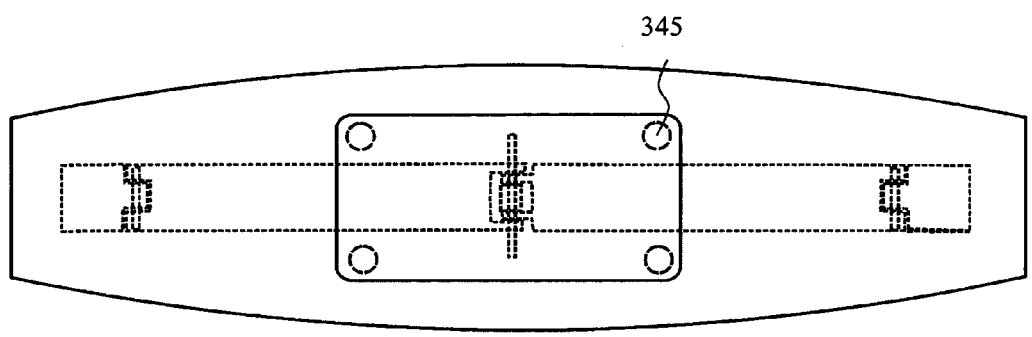
FIG. 17 is a top view of the fourth embodiment of the invention.

The fourth embodiment of the invention is shown schematically on FIGS. 16 and 17. It includes a further modification of the pair of release buttons 341 now positioned in the center of the grip right under the palm of the operator. The main feature of this release system is that centrally located release buttons 341 control two sets of levers located opposite each other, one in the front of the handgrip and the other in the back. Therefore, as many as 4 levers grip the shaft of the colonoscope both in the front and in the back, which further reduces the chance of slipping even when the shaft is wet. As in previous embodiments, the springs 345 support each release button in its engaged or "normally closed" position making the device disengaging the shaft only when the release buttons 341 are depressed.

DETAILED DESCRIPTION OF THE FIFTH PREFERRED EMBODIMENT OF THE INVENTION

This embodiment is similar to the previous embodiments with the main difference being the use of an elastic single-use protective sheath 400 designed to protect the handgrip of the invention 20 from contamination during use. This additional element (protective sheath 400) may be used with all embodiments of the invention.

Figure 18A:
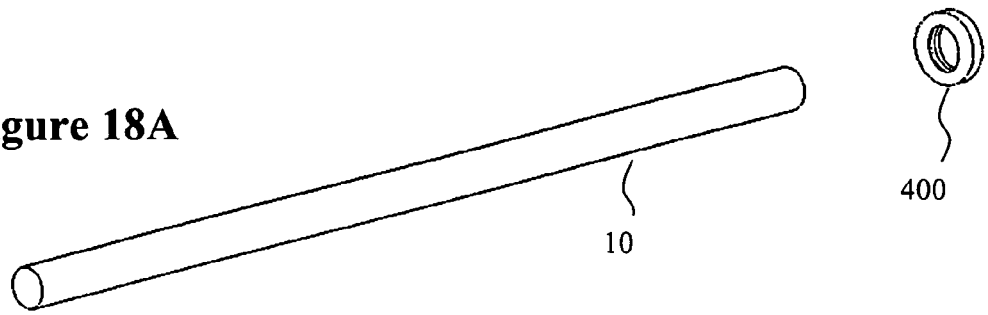
FIGS. 18A through 18E is a succession of illustrations showing the use of protective elastic cover constituting the fifth embodiment of the invention.
Figure 18B:
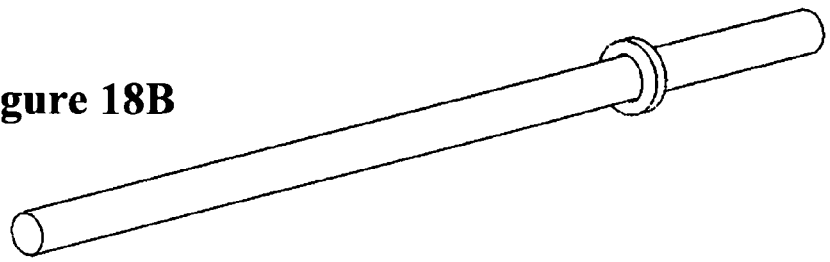
Figure 18C:
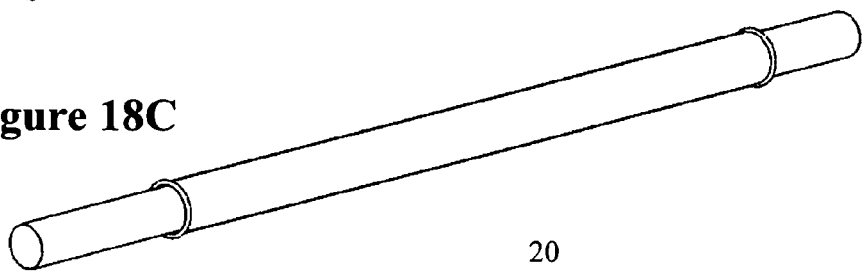
Figure 18D:
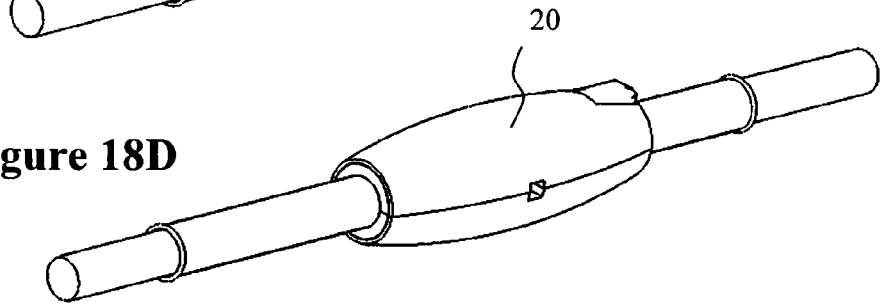
Figure 18E:
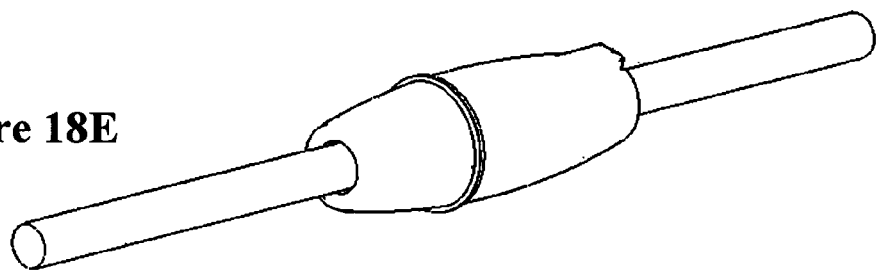

FIG. 18A shows the first step in the use of this embodiment illustrating the colonoscope shaft 10 and a sheath 400 rolled into a ring. FIG. 18B shows the ring placed onto the shaft followed by unfurling the sheath over the shaft shown on FIG. 18C. FIG. 18D shows the handgrip of the invention positioned over the sheath 400 and thus separated with a thin mechanical barrier from the sterile field of the shaft. Finally, FIG. 18E shows the ends of the sheath 400 folded over the handgrip 20 to form a complete envelope about it.

Figure 19:
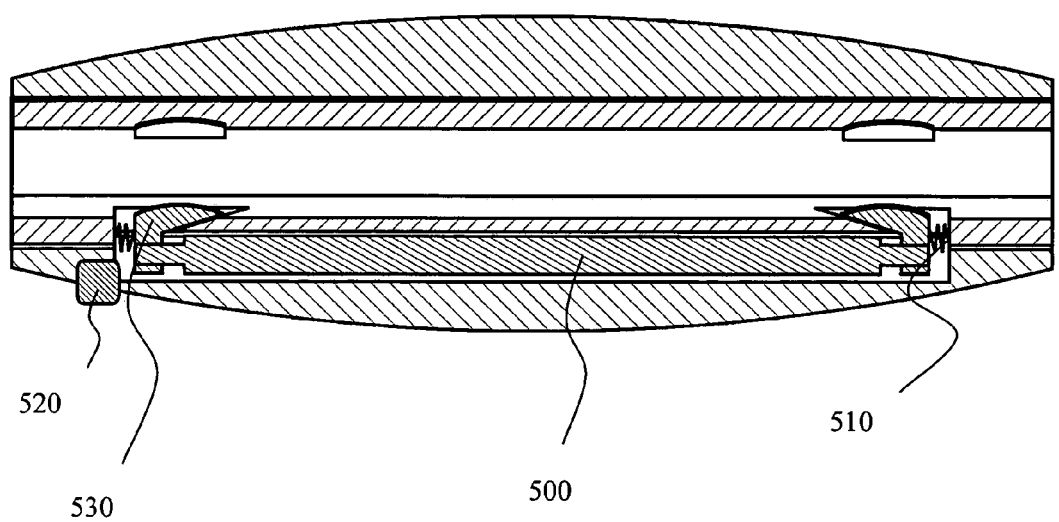
FIG. 19 is an alternate design of the engaging mechanism for the colonoscope shaft.

Finally, FIG. 19 shows an alternate design of the release button of the handgrip, which can be used with any of the above described embodiments of the invention. In order to reduce the physical force needed for activation of the release button, this design incorporates a pair of front and rear wedges 530. The wedges 530 can be brought closer to each other by a linear actuator 500 controlled by a button 520 such that the shaft of the colonoscope is wedged in its current position. When the actuator 500 releases the wedges 530 they are pulled apart by the optional return springs 510 to release the shaft of the colonoscope (not shown) from the handgrip of the invention. Piezoelectric linear actuator can be used as actuator 500. Alternately, a small electrical motor driving a worm gear set can also be used for that purpose.

The handgrip of the invention allows for the following desirable features and benefits:

Ability to maintain the position of the hand over the shaft of the colonoscope with minimal distortion, Ability to advance, turn and grip the scope to facilitate completion of the procedure with minimal distraction, Capability of engaging and disengaging to and from the scope rapidly so that the handgrip can slide along the shaft of the colonoscope, Ability to measure pull/push and torque forces in a standard rubber colon model, Easily interpretable computer representation of force and force direction, Time-stamped recording with ability to record operator-defined events, Capability of sustaining high level of disinfection or sterilization without change in sensing properties.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A handgrip for a colonoscope shaft comprising:
   an internal sleeve adapted to be placed over and engaged with said colonoscope shaft,
   an external sleeve slidingly positioned about the internal sleeve, and
   an engaging means positioned between said internal and external sleeves, said engaging means further equipped with a sensor means to measure the force applied between said external and said internal sleeves.

2. The handgrip as in claim 1, wherein said internal sleeve comprising two internal halves and an internal hinge, said external sleeve comprising two external halves, an external hinge, and an external clamp, whereby permitting side loading of said handgrip over said colonoscope shaft.

3. The handgrip as in claim 1 further including a release button imbedded in said internal sleeve and equipped with a retention lever for releasingly engaging with said colonoscope shaft.

4. The handgrip as in claim 3, wherein said release button is exposed through said external sleeve for easy activation, said release button defines an engaged position and a released position, said release button is supported by a spring in said engaged position when not depressed.

5. The handgrip as in claim 4, wherein said retention lever has an engaging surface facing said colonoscope shaft, said surface being rough for better retention of said shaft.

6. The handgrip as in claim 1, wherein said external and internal sleeves contain each an external and an internal depression, said two depressions located opposite each other, said engaging means is a rectangular bar, said sensor means are two pairs of strain gages attached to the sides of said bar, said bar positioned in and retained by said two depressions in said external and said internal sleeves.

7. The handgrip as in claim 1 further equipped with a suspension system for said internal sleeve inside said external sleeve, said suspension system comprising a front set of at least three ball bearings and a rear set of at least three ball bearings.

8. The handgrip as in claim 1 further including a pair of release buttons positioned opposite each other, each release button hingedly connected with at least one retaining lever for releasingly engaging with said colonoscope shaft.

9. The handgrip as in claim 8, wherein one of said retaining levers is concave while the other is convex to form a depression for retention of said colonoscope shaft.

10. The handgrip as in claim 8, wherein each of said release buttons defines an engaged position and a released position, each said release button is supported by a spring in said engaged position when not depressed, whereby said handgrip is engaged with said colonoscope shaft.

11. The handgrip as in claim 8 further including having each of said release buttons hingedly connected to two retaining levers located at the opposite ends of said handgrip.

12. The handgrip as in claim 1 further including an elastic single-use protective sheath adapted to be folded over said handgrip and separate thereof from said colonoscope shaft, whereby said handgrip is protected from contamination during use.

13. The handgrip as in claim 1, wherein said engaging means comprising in combination at least one radial engaging plate and at least one longitudinal engaging plate, said radial engaging plate positioned across the general direction of said colonoscope shaft and imbedded between said external sleeve and said internal sleeve, said longitudinal engaging plate positioned along the general direction of said colonoscope shaft and also imbedded between said external sleeve and said internal sleeve, said radial and longitudinal plates equipped with sensors to measure their corresponding deflection.

14. The handgrip as in claim 13, wherein said sensors are strain gage sensors.

15. The handgrip as in claim 13, wherein said engaging means comprising two radial engaging plates and two longitudinal engaging plates, said plates positioned at the opposing ends of said handgrip.

16. The handgrip as in claim 13, wherein said engaging means comprising a front set of two front radial engaging plates and two front longitudinal engaging plates, said engaging means further comprising a rear set of two rear radial engaging plates and two rear longitudinal engaging plates, all of these plates equipped with sensors to measure their corresponding deflection.

17. The handgrip as in claim 1 further including a colonoscope shaft engaging mechanism imbedded in said internal sleeve, said shaft engaging mechanism comprising a linear actuator operably engaged with a wedge means for releasingly engaging with said colonoscope shaft.

18. A handgrip system for measuring of forces applied to a colonoscope incorporating a colonoscope shaft, said system comprising:
   a handgrip comprising in turn an internal sleeve adapted to be placed over and temporarily engage with said colonoscope shaft, an external sleeve slidingly positioned about the internal sleeve, and an engaging means positioned between said internal and external sleeves, said engaging means further equipped with a sensor means to measure the forces applied between said external and said internal sleeves and provide a force data,
   an electronic unit for initial data processing, said electronic unit including a cable for transmission of said force data from said sensor means to said electronic unit, and
   a display for presentation of force data captured by said sensor means.

19. The handgrip system as in claim 18, wherein said colonoscope further incorporating an image display and wherein said display for presentation of force data is incorporated with said image display.

20. The handgrip system as in claim 18, wherein said force data is displayed on said colonoscope image display.

* * * * *

UNITED STATES PATENT AND TRADEMARK OFFICE
CERTIFICATE OF CORRECTION

| | | |
|---|---|---|
| PATENT NO. | : 6,981,945 B1 | Page 1 of 1 |
| APPLICATION NO. | : 10/986662 | |
| DATED | : January 3, 2006 | |
| INVENTOR(S) | : A. P. Sarvazyan, L. Y. Korman and S. Tsyuryupa | |

It is certified that error appears in the above-identified patent and that said Letters Patent is hereby corrected as shown below:

Col. 1, line 4 in the specification: insert before the words "BACKGROUND OF THE INVENTION" the following text:

STATEMENT REGARDING FEDERALLY SPONSORED RESEARCH OR DEVELOPMENT

This invention was made with government support under SBIR grant R44DK068936 awarded by National Institute of Diabetes and Digestive and Kidney Diseases, National Institutes of Health. The government has certain rights in the invention.

Signed and Sealed this

Second Day of December, 2008

JON W. DUDAS
*Director of the United States Patent and Trademark Office*